United States Patent [19]

Del Rossi et al.

[11] Patent Number: 5,371,314
[45] Date of Patent: Dec. 6, 1994

[54] CATALYTIC ISOPARAFFIN-OLEFIN ALKYLATION WITH HF AND A LOW DONCITITY SOLVENT

[75] Inventors: Kenneth J. Del Rossi, Woodbury, N.J.; Albin Huss, Jr., Chadds Ford, Pa.

[73] Assignee: Mobil Oil Corporation, Fairfax, Va.

[21] Appl. No.: 6,905

[22] Filed: Jan. 21, 1993

Related U.S. Application Data

[63] Continuation-in-part of Ser. No. 719,274, Jun. 21, 1991, abandoned, and a continuation-in-part of Ser. No. 856,270, Mar. 23, 1992, which is a continuation-in-part of Ser. No. 719,879, Jun. 21, 1991, abandoned.

[51] Int. Cl.$^5$ ................................................ C07C 2/62
[52] U.S. Cl. ...................................... 585/724; 585/725
[58] Field of Search ................................ 585/724, 725

[56] References Cited

U.S. PATENT DOCUMENTS

| | | | |
|---|---|---|---|
| 2,406,954 | 9/1946 | Linn | 585/724 |
| 3,778,489 | 12/1973 | Parker | 585/724 |
| 4,058,575 | 11/1977 | Cahn et al. | 585/724 |
| 5,159,129 | 10/1992 | Elmer et al. | 585/717 |
| 5,196,628 | 3/1993 | Del Rossi et al. | 585/725 |
| 5,202,518 | 4/1993 | Del Rossi | 585/724 |
| 5,220,096 | 6/1993 | Del Rossi | 585/724 |

*Primary Examiner*—Asok Pal
*Attorney, Agent, or Firm*—Alexander J. McKillop; Dennis P. Santini; Robert B. Furr, Jr.

[57] ABSTRACT

The invention provides an isoparaffin-olefin alkylation catalyst composition comprising from about 5 to about 95 weight percent hydrofluoric acid, from about 5 to about 95 weight percent of a solvent having a Donor Number of less than about 40 and from about 0.05 to about 10 weight percent water.

An isoparaffin-olefin alkylation process employing the catalyst composition of the invention is also disclosed.

6 Claims, No Drawings

CATALYTIC ISOPARAFFIN-OLEFIN ALKYLATION WITH HF AND A LOW DONCITITY SOLVENT

CROSS-REFERENCE TO RELATED APPLICATION

This application is a continuation-in-part of U.S. application Ser. No. 07/719,274, filed Jun. 21, 1991, now abandoned, and of U.S. application Ser. No. 07/856,270, filed Mar. 23, 1992, which is a continuation-in-part of application Ser. No. 07/719,879, filed Jun. 21, 1991, now abandoned.

FIELD OF THE INVENTION

The present invention relates to the art of catalytic alkylation. More specifically, the invention relates to a liquid alkylation catalyst and an isoparaffin-olefin alkylation process. Particularly, the invention provides a liquid alkylation catalyst composition which avoids many of the safety and environmental concerns associated with hydrofluoric acid while retaining a commercially useful level of isoparaffin-olefin alkylation catalytic activity.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used concentrated hydrofluoric or sulfuric acid catalysts under relatively low temperature conditions. Acid strength is preferably maintained at 88 to 94 weight percent by the continuous addition of fresh acid and the continuous withdrawal of spent acid. As used herein, the term "concentrated hydrofluoric acid" refers to an essentially anhydrous liquid containing at least about 85 weight percent HF.

Hydrofluoric and sulfuric acid catalyzed alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381–397, (1988). For a survey of hydrofluoric acid catalyzed alkylation, see 1 *Handbook of Petroleum Refining Processes* 23–28 (R.A. Meyers, ed., 1986).

Hydrogen fluoride, or hydrofluoric acid (HF) is highly toxic and corrosive. However, it is used as a catalyst in isomerization, condensation, polymerization and hydrolysis reactions. The petroleum industry used anhydrous hydrogen fluoride primarily as a liquid catalyst for alkylation of olefinic hydrocarbons to produce alkylate for increasing the octane number of gasoline. Years of experience in its manufacture and use have shown that HF can be handled safely, provided the hazards are recognized and precautions taken. Though many safety precautions are taken to prevent leaks, massive or catastrophic leaks are feared primarily because the anhydrous acid will fume on escape creating a vapor cloud that can be spread for some distance. Previous workers in this field approached this problem from the standpoint of containing or neutralizing the HF cloud after its release.

U.S. Pat. No. 4,938,935 and U.S. Pat. No. 4,985,220 to Audeh and Greco, as well as U.S. Pat. No. 4,938,936 to Yan teach various methods for containing and/or neutralizing HF acid clouds following accidental releases.

But it would be particularly desirable to provide composition which avoids the cloud forming problems associated with HF while providing commercially useful activity as an isoparaffin-olefin alkylation catalyst. Diluents and complexing agents for hydrofluoric acid have, in the past, been disclosed for various purposes as noted in the following references.

U.S. Pat. No. 2,615,908 to McCaulay teaches thioether-HF-copper complex compounds and a method for preparing the same. Potential uses for the thioether-HF-copper composition compounds are listed from column 6, line 55 through column 8 at line 3. The method is said to be useful for purifying HF-containing vent gases from an industrial HF alkylation plant. See column 7, lines 10–24.

U.S. Pat. No. 3,531,546 to Hervert discloses a HF-$CO_2$ catalyst composition which is said to be useful for alkylation as well as olefin isomerization.

U.S. Pat. No. 3,795,712 to Torck et al. relates to acid catalysts comprising a Lewis acid, a Bronsted acid, and a sulfone of the formula R—$SO_2$—R', where R and R' are each separately a monovalent radical containing from 1 to 8 carbon atoms or form together a divalent radical having from 3 to 12 carbon atoms.

U.S. Pat. No. 3,856,764 to Throckmorton et al. teaches an olefin polymerization catalyst comprising (1) at least one organoaluminum compound, (2) at least one nickel compound selected from the class consisting of nickel salts of carboxylic acids, organic complex compounds of nickel, or nickel tetracarbonyl and (3) at least one hydrogen fluoride complex prepared by complexing hydrogen fluoride with a member of the class consisting of ketones, ethers, esters, alcohols, nitriles, and water.

U.S. Pat. No. 4,636,488 discloses an anhydrous nonalcoholic alkylation catalyst comprising a mixture of a mineral acid and an ether in proportions of from about 50 to about 99 weight percent of mineral acid and from about 1 to about 50 weight percent of ether. Useful mineral acids include HF; see column 4 at lines 56–60.

Promoters such as alcohols, thiols, water, ethers, thioethers, sulfonic acids, and carboxylic acids are disclosed in combination with strong Bronsted acids such as HF, fluorosulfonic and trihalomethanesulfonic acids in U.S. Pat. No. 3,778,489 to Parker et al. The promoters are said to modify the activity of the strong Bronsted acids for alkylation.

U.S. Pat. No. 3,795,712 to Torck et al. teaches hydrocarbon alkylation in the presence of a sulfone and from $10^{-5}$ to 5 moles of hydroiluoric acid per liter of sulfone.

U.S. Pat. No. 4,025,577 and U.S. Pat. No. 4,094,924 to Siskin et al. teach isoparaffin-olefin alkylation catalysts comprising a hydrogen halide and a metal fluoride, and, optionally, a suitable diluent.

The preceding references demonstrate the desirability of a liquid Bronsted acid catalyst (such as HF) for isoparaffin-olefin alkylation, as well the utility of liquid Bronsted acids in combination with metal halides, particularly metal fluorides. However, metal fluorides have been found to cause operational problems in two principal areas. First, the corrosovity of metal halides toward materials of process unit construction is of a character sufficiently distinct from that of the strong Bronsted acids that more costly preventive measures (including alloy selection, coating, and additive treatment) are required. Second, the presence of a metal halide in a liquid alkylation catalyst composition complicates process design and increases capital and operating costs for the catalyst recovery, treatment, and recycle facilities. Thus, it would be highly desirable both from the standpoint of initial process design and unit construction, as well as from the standpoint of operational simplicity and reliability, to provide an alkylation catalyst composition and process which avoids both the safety and environmental concerns associated with concentrated HF while also overcoming the design and operational difficulties attendant to the use of intentionally added metal halides. Allowed U.S. application Ser. No. 07/856,270, filed Mar. 23, 1992, disclosed a method for decreasing the corrosivity of mixtures of HF and sulfolane comprising adding a controlled amount of water to the HF/sulfolane mixture. U.S. application Ser. No. 07/719,274, now abandoned, disclosed mixtures of strong Bronsted acids and solvents having Donor Numbers of less than about 40. Mixtures of hydrofluoric acid and one or more of these solvents were particularly promising as safer alternatives to concentrated HF for isoparaffin-olefin alkylation, but were found to be corrosive toward carbon steel.

SUMMARY OF THE INVENTION

This invention provides a method for decreasing the corrosivity of mixtures of HF and a particular class of solvents. In accordance with the present invention, it has been found that the controlled addition of water to mixtures containing solvents having Donor Numbers less than about 40 and hydrofluoric acid surprisingly decreases the corrosivity of the hydrofluoric acid/solvent mixture.

The invention provides, in a first aspect, an alkylation catalyst complex comprising from about 5 to about 95 weight percent hydrofluoric acid, from about 5 to about 95 weight percent of a solvent having a Donor Number of less than about 40 and from about 0.5 to about 10 weight percent water in the absence of added metal halide.

The invention further provides, in a second aspect, a process for alkylating an isoparaffin with an olefin comprising effecting reaction of isoparaffin and olefin with an alkylation catalyst composition comprising from about 5 to about 95 weight percent of hydrofluoric acid, from about 5 to about 95 weight percent of a solvent having a Donor Number of less than about 40, and from about 0.5 to about 10 weight percent water in the absence of added metal halide.

DETAILED DESCRIPTION

The invention provides a liquid isoparaffin-olefin alkylation catalyst composition which provides commercially useful levels of isoparaffin-olefin alkylation activity while avoiding safety and environmental concerns attendant to the storage, transfer, and processing of concentrated HF. Further, the invention reduces the corrosivity of the HF/solvent mixture to assure safe operation with economical carbon steel process equipment.

Feedstocks

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, isopentane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, hexene, octene, and heptene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44–56, the disclosure of which is incorporated by reference as if set forth at length herein.

The molar ratio of isoparaffin to olefin is generally from about 1:1 to about 100:1, preferably from about 1:1 to about 50:1, and more preferably from about 5:1 to about 20:1.

Additive Donor Number

The term "donicity" describes the propensity of a solvent to donate electron pairs to acceptor solutes. The term "Donor Number" (DN) as used herein is a measure of donicity, and is defined as the negative of the enthalpy change, measured in Kcal·mol$^{-1}$, for the reaction of the solvent with $SbCl_5$ to form a 1:1 adduct, where both reactants are in dilute solution in 1,2-dichloroethane (DCE). For a discussion of donicity and Donor Numbers, see Y. Marcus, "The Effectivity of Solvents as Electron Pair Donors", 13 *Journal of Solution Chemistry* 599 (1984). Table A below, reports donor numbers listed in the Marcus article for various solvents.

Additives useful in the present invention include nitroalkanes, carbonates, perhalogenated alkanes, halogenated alcohols, sulfonic acids, sulfones, acetyl halides, benzoyl halides, phosphorous oxychloride, alkyl sulfites, anhydrides, esters, and sulfuryl halides. Nonlimiting examples of these additives include nitromethane, 1-nitropropane, propylene carbonate, perfluorodecalin, 2,2,2-trifluoroethanol, methanesulfonic acid, sulfolane, acetyl chloride, benzoyl fluoride, methyl propionate, sulfuryl chloride, and sulfuryl chloride fluoride.

TABLE A

| Solvent | DN | Solvent | DN |
|---|---|---|---|
| 1,2-dichloroethane | (0) | Methyl-t-butylketone | 17.0 |
| Acetyl Chloride | 0.7 | Diethyl Ether | 19.2 |
| Benzoyl Chloride | 2.3 | Tetrahydrofuran | 20.0 |
| Sulfuryl Chloride | 0.1 | Triethylamine | 30.5 |
| Thionyl Chloride | 0.4 | Pyridine | 33.1 |
| Selenoyl Chloride | 12.2 | Acetonitrile | 14.1 |
| Phosphoryl Chloride | 11.7 | Propanonitrile | 16.1 |
| Tetrachloroethylene Carbonate | 0.8 | Butanonitrile | 16.6 |
|  |  | Isobutanonitrile | 15.4 |
| Dichloroethylene Carbonate | 2.7 | Benzyl Cyanide | 15.1 |
|  |  | Benzonitrile | 11.9 |
| Nitromethane | 2.7 | N,N-Dimethylformamide | 26.6 |
| Nitrobenzene | 4.4 | N,N-Diethylformamide | 30.9 |
| Acetic Anhydride | 10.5 | N,N-Dimethylacetamide | 27.8 |
| Methyl Acetate | 16.4 | N,N-Diethylacetamide | 32.2 |
| Ethyl Acetate | 17.1 | etramethyl Urea | 29.6 |
| 2-Propyl Acetate | 17.5 | Hexamethyl Phosphoric |  |
| Ethyl Propanoate | 17.1 | Triamide | 38.8 |
| Ethyl Butanoate | 16.8 | Ethylene Sulfite | 15.3 |
| Ethyl Isobutanoate | 16.4 | Dimethylsulfoxide | 29.8 |
| Ethyl t-Pentanoate | 12.9 | Tetramethylene Sulfone | 14.8 |

TABLE A-continued

| Solvent | DN | Solvent | DN |
| --- | --- | --- | --- |
| Diethylcarbonate | 16.0 | Phenyldifluorophosphine Oxide | 16.4 |
| Ethylene Carbonate | 16.4 | | |
| 1,2-propylene Carbonate | 15.1 | Phenyldichlorophosphine Oxide | 18.5 |
| Acetone | 17.0 | Diphenylchlorophosphine Oxide | 22.4 |
| 2-Butanone | 17.4 | | |
| Methylisopropyl-ketone | 17.1 | Trimethyl Phosphate | 23.0 |
| | | Tri-n-butyl Phosphate | 23.7 |

Thus additives useful in the present invention are characterized by Donor Numbers of less than about 40, preferably less than about 30, more preferably less than about 16.

Water Addition

The present invention requires adding water to the HF/solvent mixture to provide a final mixture containing from about 0.5 to about 10 weight percent water, preferably from about 0.5 to about 5.0 weight percent water, and more preferably from about 0.5 to about 2.0 weight. When the HF/solvent mixture is used as a catalyst for isoparaffin-olefin alkylation, the necessary water content may be maintained by adding water to the circulating catalyst. Depending upon the particular solvent used (and its affinity for water) significant amounts of make-up water may or may not be required.

Process Conditions

The catalyst composition of the present invention may be readily substituted for the concentrated hydrofluoric acid catalyst in an existing hydrofluoric acid alkylation process without substantial equipment modifications. Specifically, existing carbon steel equipment is compatible with the composition of the invention and replacement with higher alloys is unnecessary. Accordingly, the conversion conditions for the process of the present invention resemble those of typical commercial hydrofluoric acid alkylation processes.

The present alkylation process is suitably conducted at temperatures of from about 10° to about 500° C., preferably from about 10° to about 200° C., and more preferably from about 20° C. to about 60° C. Pressure is maintained to ensure a liquid phase in the alkylation reaction zone. Pressures typically range from about 20 to about 1200 psig, preferably from about 50 to about 500 psig. Olefin feed rates generally range from about 0.01 to about 10 WHSV and more preferably from about 0.05 to about 5 $hr^{-1}$ WHSV. The mixed isoparaffin-olefin reactants may be contacted with the catalyst composition of the invention in any suitable reaction vessel, examples of which include stirred-tank rejectors as well as riser-type reactors. Contact time for the mixed isoparaffin-olefin feed and the catalyst composition of the invention typically are within the range of from about 0.1 second to about 100 minutes, and more preferably from about 10 seconds to about 20 minutes.

The low donicity solvent component of the alkylation catalyst composition may be added by injection directly into the alkylation process unit, or may be mixed with the hydrocarbon charge, or may be mixed with the fresh and/or the circulating acid catalyst component, or with a stream of mixed acid/additive catalyst. The HF and the low donicity solvent must be mixed in the presence of water if carbon steel mixing equipment is used. Alternatively, the HF/solvent mixture may be prepared, stored, and transferred in corrosion-resistant alloy equipment up to and including the completion of the water addition step. Downstream from the alkylation reaction zone, the low donicity solvent is preferably separated from the alkylate product stream, mixed with fresh and/or circulating acid and/or circulating acid/additive catalyst mixture, and recycled to the alkylation reaction zone. The particular separation technique selected, however, depends upon the characteristics of the selected solvent.

The low donicity solvent may partition between the acid and the alkylate-containing hydrocarbon reactor effluent, or may remain in either the hydrocarbon or the acid phase, or may form a third discrete phase, depending upon the characteristics of the selected low donicity solvent. If the boiling point of the selected low donicity solvent does not overlap major hydrocarbon products, distillation is preferred to separate and recycle the solvent. Higher boiling (e.g. >2° C.) solvents may require extraction (for example, liquid-liquid solvent extraction) to be efficiently recovered from alkylation byproducts such as ASO (acid soluble oil).

EXAMPLES

The following Examples demonstrate both the effectiveness of the solvent-containing catalyst composition of the invention for catalyzing isoparaffin-olefin alkylation as well as the present method for decreasing the corrosivity of these mixtures. Example 1 demonstrates the well-known effectiveness of anhydrous HF as an isoparaffin-olefin alkylation catalyst.

Example 1

Comparative

Anhydrous HF (40 grams, obtained from Matheson Chemical Company of Bridgeport, N.J.) was condensed into a clean, dry autoclave (1000 cc). Isobutane (100 grams) was added, and the autoclave was stirred at 1500 rpm. The autoclave was brought to room temperature (22° C., 71° F.) and pressurized to 100 psig. A pre-mixed 10:1 weight: weight mixture of isobutane: 2-butene feed (obtained from Matheson Chemical Company) was added at a rate of 250 cc/hour for 2 hours under autogeneous pressure for a total isobutane: 2-butene charge of 500 cc. A 10°–15° F. (5°–8° C.) temperature rise was observed during feed addition resulting in an average reaction temperature of 27°–30° C. (80°–85° F.). The autoclave was sampled (300 cc) immediately after feed addition was complete. The sample was flashed at room temperature and quenched with a chilled water trap. Samples of the liquid and gas products were analyzed by capillary GC (60m DB-1 column). The results of Example 1 are shown in the Table B below.

Examples 2–4

The following procedure was followed for Examples 2–4. In a typical experiment, 10 grams of sulfolane (tetramethylene sulfone, Phillips Petroleum Co.) was loaded into a clean, dry 1000 cc autoclave. Sulfolane (characterized by a Donor Number of about 14.8) was stored in a vacuum desiccator over $P_2O_5$ prior to use. The autoclave was sealed and cooled with liquid nitrogen. The autoclave was evacuated and 40 grams of anhydrous HF (Matheson) were condensed into the autoclave. The HF/sulfolane mixture was warmed to room temperature (71° F.). Isobutane (100 grams) was added to the mixture, the autoclave was pressurized to 100 psig and stirred at 1500 rpm. A pre-mixed 10/1 wt/wt isobutane/2-butene feed (Matheson) was then introduced at 250 cc/hr. A 5°–10° F. temperature rise was typically observed during reaction. After two hours, feed addition was halted and a 300 cc liquid sample was obtained. The liquid sample was depressured through an ice cooled trap (filled with 50 cc of water) which was connected to a gas sampling bomb and wet test meter. The liquid alkylate product and gas sample were analyzed with a Varian 6000 gas chromatograph equipped with a 60 meter DB-1 capillary column.

Table B below lists the results with HF/sulfolane mixtures containing up to 50 wt % sulfolane in HF. With 20 wt % sulfolane in HF (125 moles HF per liter sulfolane), performance was comparable to pure HF. The ratio of high octane trimethylpentanes to lower octane dimethylhexanes (TMP/DMH) was 9.4 with 80/20 HF/sulfolane compared to 9.2 with pure HF. Performance diminished slightly upon adding 50 wt % sulfolane to HF (63 moles HF per liter of sulfolane). Alkylate with 50/50 HF/sulfolane catalyst had a TMP/DMH ratio of 6.5 and contained 11.8 wt % $C_9+$. A 40/60 HF/sulfolane catalyst (42 moles of HF per liter of sulfolane) showed no activity for alkylation. The only observed product was butyl fluoride formed by hydrofluorination of 2-butene feed. Thus, the useful concentration range for sulfolane in HF was shown to be below about 60 wt % in HF (greater than about 40 moles of HF per liter of sulfolane).

Alkylate quality increased slightly upon adding 20 wt % sulfolane to HF ($C_5$+MON 97.5 vs 97 for pure HF), then decreased with further sulfolane dilution. Activity for isoparaffin/olefin alkylation was not observed above about 50 wt % sulfolane in HF.

TABLE B

| Example | 1 | 2 | 3 | 4 |
|---|---|---|---|---|
| Catalyst | HF | HF/Sulfolane | HF/Sulfolane | HF/Sulfolane |
|  | (80/0) | (60/40) | (50/50) |  |
| Appearance | Fuming | Fuming | Liquid | Liquid |
| Alkylate Product wt % |  |  |  |  |
| $C_5$—$C_7$ | 5.5 | 4.7 | 5.9 | 8.3 |
| $C_8$ | 88.1 | 89.3 | 85.5 | 79.9 |
| $C_9+$ | 6.4 | 6.0 | 8.6 | 11.8 |
| TMP/DMH | 9.2 | 9.4 | 7.5 | 6.5 |
| Olefin Conv., % | 99.9 | 100 | 98.0 | 98.8 |

Examples 5-8

Experimental Procedure

Mixtures of HF and sulfolane were evaluated for their corrosivity toward carbon steel in accordance with the following procedure.

Sulfolane (tetramethylene sulfone as received from Aldrich Chemical Company) was vacuum distilled twice from KOH and once from CaH. The dried sulfolane was stored in a vacuum dessicator over $P_2O_5$.

In a typical experiment, a carbon steel rod (5.25" long, 0.25" diameter) was attached to a teflon connector to the top of a 300 cc stainless steel autoclave (fabricated by Autoclave Engineers, Inc.). Purified sulfolane (49.5 grams) and deionized water (1 gram) were added to the autoclave under a nitrogen atmosphere. The autoclave was sealed, cooled with liquid nitrogen, and evacuated with a rough vacuum. HF (60 grams, Matheson) was condensed into the autoclave. The cold autoclave was connected to a pilot unit equipped with a LPG feed system and acid scrubber. The autoclave was warmed to 85° F., pressurized to 100 psig with isobutane (Matheson), and stirred at 100 rpm. The contents were purged with 280 cc/hr of isobutane for 24 hours. The isobutane purge was removed and the autoclave was sealed for 150 hours at 85° F. and 100 psig. HF loss during the isobutane purge was estimated at 10 grams, thus the purged mixture sealed for 150 hours was roughly 50/49/1 wt./wt./wt. HF/sulfolane/$H_2O$.

At the end of the corrosion experiment, the autoclave was vented through caustic scrubbers, and opened in a fume hood. The carbon steel rod was removed, rinsed with acetone and stored in a dessicator. The bottom portion (1 inch) of the carbon steel rod that was immersed in the HF/sulfolane catalyst developed a protective coating. The protective film was removed with a mechanical bead blaster to expose the non-corroded metal. The corrosion rate was determined from the measured decrease in rod thickness.

Results from Examples 5-8 are shown in Table E.

TABLE E

| Carbon Steel Corrosion Data | | | |
|---|---|---|---|
| Experiment # | Wt % $H_2O$ in Catalyst @ t = o | Corrosion Rate mils/yr | Comments |
| 5 | 0.5 | 636 | Severe |
| 6 | 1.0 | 25 | Mild, uniform |
| 7 | 2.0 | 3 | Low, uniform |
| 8 | 4.2 | 6 | Low, uniform |

Example 9

An HF/methanesulfonic acid catalyst composition was evaluated for isoparaffin/olefin alkylation with a 10/1 wt/wt isobutane/2-butene feed at 76°–80° F. in a semi-batch autoclave. The Donor Number of methanesulfonic acid is less than 10. In Example 31, 10 grams of methanesulfonic acid (Aldrich Chemical Co.) was added to a clean, dry autoclave (1000 cc). The autoclave was sealed, cooled with liquid nitrogen and placed under vacuum. Anhydrous HF (40 grams, Matheson) was then condensed into the autoclave. Isobutane (100 grams) was added, and the autoclave was stirred at 1500 rpm. The autoclave was brought to room temperature 21° C. (70° F.) and pressurized to 100 psig. A premixed 10/1 wt/wt isobutane/2-butene feed (Matheson) was then added (500 cc at a rate of 250 cc/hr) under autogenous pressure. A 4°–7° C. (8°–12° F.) temperature rise was observed during feed addition resulting in an average reaction temperature of 26°–28° C. (79°–83° F.). The autoclave was sampled (300 cc) immediately after feed addition was complete. The sample was flashed at room temperature and quenched with a chilled water trap. Samples of the liquid and gas products were analyzed by capillary GC (60 m DB-1 column). Results are summarized in Table I, below.

Examples 10-12

The procedure of Example 9 was repeated in Examples 10-12 with 26.7, 60, and 160 grams of methanesulfonic acid, respectively. Results for Examples 9-12 are reported in Table F, below.

TABLE F

| Results With HF/MSA Catalysts | | | | |
|---|---|---|---|---|
|  | Example 9 | Example 10 | Example 11 | Example 12 |
| Mol % MSA in HF | 5.0 | 12.2 | 23.8 | 45.5 |

TABLE F-continued

Results With HF/MSA Catalysts

| | Example 9 | Example 10 | Example 11 | Example 12 |
|---|---|---|---|---|
| Butene Conversion, wt % | 99.3 | 100 | 99.3 | 98.0 |
| C8 paraffin Yield, wt % | 83.1 | 75.9 | 76.3 | 55.7 |

Table F lists the results with HF/MSA catalysts containing up to 46 mol % MSA. Butene conversion remained above 98% for the entire range of HF/MSA catalysts tested. Yield of $C_8$ paraffins (primary alkylation products) fell from 88 wt % with pure HF to 56 wt % with a catalyst containing 46 mol % MSA in HF. Butyl fluoride was not detected in the products. This result shows that methanesulfonic acid has little impact on the acid activity of HF.

Examples 13 and 14

Examples 13 and 14 describe corrosion tests with an anhydrous HF/methanesulfonic acid mixture (50/50 wt %), and a wet HF/methanesulfonic acid mixture (49/49 wt % with 2 wt % H20 added), respectively. Analogous to results with anhydrous HF/sulfolane, added water significantly reduced the corrosivity of the liquid }IF/solvent mixture.

Carbon steel coupons (length=5 cm, width=1.5, height=0.3 cm) were mounted on a 316 stainless steel rack. The coupons were insulated from the rack with Teflon washers. The rack was placed in bottom of a 1000 cc stainless steel Parr autoclave, and the entire apparatus was moved into a nitrogen-filled glove bag. Methanesulfonic acid (50 grams, Aldrich Chemical Company) was added to the autoclave in the glove bag, and the autoclave was sealed. The autoclave was chilled and evacuated to 20 torr. Anhydrous hydrofluoric acid (50 grams, Matheson) was condensed into the autoclave- The contents were warmed to 85° F. and isobutane (200 grams, Matheson) was added to the autoclave. The isobutane was added to simulate actual alkylation unit conditions. It should be noted that the carbon steel coupons were submersed in the heavy acid phase within the autoclave. The autoclave was pressured to 100 psig with nitrogen and stirred at 500 rpm. The experiment was continued at 85° F., 500 rpm stirring and autogenous pressure. After 4 days on-stream, the autoclave was vented into caustic traps, and purged with nitrogen for 4 hours. The autoclave was opened in a fume hood, and the rack rinsed with acetone. The carbon steel coupons were cleaned with a mechanical bead blaster, and weighed. The corrosion rate in milli-inches/year (mpy) was determined from the coupon weight lost during the four day exposure.

The corrosion rate for carbon steel exposed to anhydrous HF/methanesulfonic acid (50/50 wt %) was measured to be 405 mpy. In contrast, the rate measured for coupons exposed to wet HF/methanesulfonic acid (49/49 wt % with 2 wt % added water) was 260 mpy.

Examples 15 and 16

HF/propylene carbonate

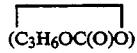
(C3H6OC(O)O)

catalysts were evaluated for isoparaffin/olefin alkylation with a 10/1 wt/wt isobutane/2-butene feed at 80° F. in a semi-batch autoclave. In Examples 15 and 16, 10 and 26.7 grams of propylene carbonate, respectively, (Aldrich Chemical Co.) were added to a clean, dry autoclave (1000 cc). The autoclave was sealed, cooled with liquid nitrogen and placed under vacuum. Anhydrous HF (40 grams, Matheson) was then condensed into the autoclave. Isobutane (100 grams) was added, and the autoclave was stirred at 1500 rpm. The autoclave was pressurized to 100 psig and brought to room temperature 22° C. (71° F.). A pre-mixed 10/1 wt/wt isobutane/2-butene feed (Matheson) was then added (500 cc at a rate of 250 cc/hr) under autogenous pressure. An 8°–12° F. (4°–7° C.) temperature rise was observed during feed addition resulting in an average reaction temperature of 26°–28° C. (79°–83° F.). The autoclave was sampled (300 cc) immediately after feed addition was complete. The sample was flashed at room temperature and quenched with a chilled water trap. Samples of the liquid and gas products were analyzed by capillary GC (60m DB-1 column).

Results from experiments conducted with pure HF and HF/propylene carbonate mixtures are given in Table G below. The HF/carbonate mixtures tested (80/20 and 60/40 wt/wt) were liquids which fumed mildly in air. The physical appearance of the HF/carbonate mixtures indicated that the vapor pressure of HF had been significantly reduced. However, alkylation performance was only slightly diminished upon adding up to 40 wt % propylene carbonate to HF. The ratio of high octane trimethylpentanes to lower octane dimethylhexanes in the alkylate product decreased slightly from 9.2 with a pure HF catalyst to 8.2 with a 80/20 wt/wt HF/propylene carbonate catalyst. Also, the amount of heavy $C_9$+alkylate increased from 6.4 wt % to only 7.0 wt % with the 80/20 catalyst. The results demonstrate the efficacy of carbonate compounds as additives for HF.

TABLE G

Semi-Batch Evaluation of HF/Propylene Carbonate

| | Example 15 | Example 16 |
|---|---|---|
| Catalyst | HF/C3H6OC(O)O (80/20 wt/wt) | HF/C3H6OC(O)O (60/40 wt/wt) |
| Appearance | Liquid | Liquid |
| HF/additive (mol/mol) | 20/1 | 8/1 |
| Alkylate product, wt. % | | |
| C5-C7 | 6.6 | 9.9 |
| C8 | 86.4 | 75.0 |
| C9+ | 7.0 | 15.1 |
| TMP/DMH | 8.2 | 6.0 |
| Olefin Conv, % | 98.8 | 97.0 |

Examples 17 and 18

Examples 17 and 18 describe corrosion tests with an anhydrous HF/propylene carbonate mixture (50/50 wt %), and a wet HF/propylene carbonate mixture (49/49 wt % with 2 wt % H20 added). Analogous to results with anhydrous HF/sulfolane and HF/methanesulfonic acid mixtures, added water significantly reduced the corrosivity of the liquid HF/solvent mixture.

The identical procedure described for examples 13 and 14 was employed to evaluate the corrosivity of HF/propylene carbonate mixtures. The corrosion rate for carbon steel exposed to anhydrous HF/propylene carbonate (50/50 wt %) was measured to be 2.7 mpy. In contrast, the rate measured for coupons exposed to wet HF/propylene carbonate (49/49 wt % with 2 wt % added water) was 2.1 mpy.

Changes and modifications in the specifically described embodiments can be carried out without departing from the scope of the invention which is intended to be limited only by the scope of the appended claims.

What is claimed is:

1. A process for alkylating as isoparaffin with an olefin comprising effecting reaction of isoparaffin and olefin with an alkylation catalyst composition comprising from about 5 to about 95 weight percent hydrofluoric acid, from about 5 to about 95 weight percent of a solvent selected from the group consisting of carbonates and nitroalkanes and from about 0.05 to about 10 weight percent water in the absence of metal halide.

2. The process of claim 1 wherein said solvent is nitromethane or 1-nitropropane.

3. The process of claim 1 wherein said solvent is propylene carbonate.

4. The process of claim 1 wherein said solvent comprises from about 10 to about 80 weight percent of said catalyst composition.

5. The process of claim 4 wherein said solvent comprises from about 20 to about 60 weight percent of said catalyst composition.

6. The process of claim 1 further comprising charging said isoparaffin and said olefin to a riser reactor containing said catalyst composition.

* * * * *

UNITED STATES PATENT AND TRADEMARK OFFICE
CERTIFICATE OF CORRECTION

PATENT NO. : 5,371,314
DATED : December 6, 1994
INVENTOR(S) : K. J. Del Rossi and A. Huss, Jr.

It is certified that error appears in the above-indentified patent and that said Letters Patent is hereby corrected as shown below:

Title page, item [54] and in column 1, line 3:
In the Title,"Doncitity" should be --Donicity--

Signed and Sealed this

Eighteenth Day of April, 1995

Attest:

BRUCE LEHMAN

Attesting Officer

Commissioner of Patents and Trademarks